(12) United States Patent
Wiesner et al.

(10) Patent No.: US 8,760,146 B2
(45) Date of Patent: Jun. 24, 2014

(54) SAFETY INTERLOCK

(75) Inventors: Joel D Wiesner, St. Peters, MO (US); Joseph A Hudson, O'Fallon, MO (US); Jason Boulanger, Trenton, IL (US)

(73) Assignee: Covidien LP, Mansfield, MA (US)

( * ) Notice: Subject to any disclaimer, the term of this patent is extended or adjusted under 35 U.S.C. 154(b) by 139 days.

(21) Appl. No.: 13/416,837

(22) Filed: Mar. 9, 2012

(65) Prior Publication Data

US 2012/0172801 A1 Jul. 5, 2012

Related U.S. Application Data

(63) Continuation of application No. 12/777,357, filed on May 11, 2010, now Pat. No. 8,154,274.

(51) Int. Cl.
*G01R 31/02* (2006.01)
*A61M 5/142* (2006.01)

(52) U.S. Cl.
USPC ............................ 324/72; 324/76.11; 604/151

(58) Field of Classification Search
USPC .................................. 324/72, 76.11; 604/151
See application file for complete search history.

(56) References Cited

U.S. PATENT DOCUMENTS

| | | | |
|---|---|---|---|
| 2,483,924 A | 10/1949 | Moulinier | |
| 3,432,128 A | 3/1969 | Elleboudt | |
| 3,435,209 A | 3/1969 | Keahl | |
| 3,523,179 A | 8/1970 | Edwards et al. | |
| 3,673,476 A | 6/1972 | Hamburg | |
| 3,675,653 A | 7/1972 | Crowley et al. | |
| 3,693,025 A | 9/1972 | Brunton | |
| 3,851,976 A | 12/1974 | Meier | |
| 3,982,162 A | 9/1976 | Olliffe | |
| 3,985,133 A | 10/1976 | Jenkins et al. | |
| 3,987,303 A | 10/1976 | Stoft et al. | |
| 3,993,061 A | 11/1976 | O'Leary | |
| 4,038,982 A | 8/1977 | Burke et al. | |
| 4,126,132 A | 11/1978 | Portner et al. | |
| 4,300,048 A | 11/1981 | Barbier et al. | |
| 4,346,296 A | 8/1982 | Passaro et al. | |
| 4,424,011 A | 1/1984 | O'Brien et al. | |

(Continued)

FOREIGN PATENT DOCUMENTS

DE 3627011 A1 2/1988
DE 3910250 A1 10/1990

(Continued)

OTHER PUBLICATIONS

Office action issued Jan. 3, 2013 regarding U.S. Appl. No. 13/211,423, 14 pgs.

(Continued)

*Primary Examiner* — Vincent Q Nguyen

(57) ABSTRACT

A safety interlock for use in a medical device having a control system for controlling operation of the medical device includes a central tubular portion defining a fluid passage for passing fluid through the safety interlock. An outer ring portion is adapted for mounting the safety interlock in the medical device. A spoked connector portion connects the central tubular portion to the outer ring portion so that the outer ring portion is spaced radially outwardly from the central tubular portion in opposed relation with at least a portion of the central tubular portion. The safety interlock is adapted for mounting in the medical device in a path of electromagnetic radiation from a source of electromagnetic radiation such that the central tubular portion reflects the electromagnetic radiation to a electromagnetic radiation detector when properly loaded on the medical device.

9 Claims, 8 Drawing Sheets

(56) References Cited

U.S. PATENT DOCUMENTS

| | | |
|---|---|---|
| 4,454,763 A | 6/1984 | Mahler |
| 4,504,263 A | 3/1985 | Steuer |
| 4,508,422 A | 4/1985 | Karlsson |
| 4,525,069 A | 6/1985 | Tanaka et al. |
| 4,537,561 A | 8/1985 | Xanthopoulos |
| 4,646,144 A | 2/1987 | Ishida et al. |
| 4,652,260 A | 3/1987 | Fenton, Jr. et al. |
| 4,665,391 A | 5/1987 | Spani |
| 4,714,463 A | 12/1987 | Archibald et al. |
| 4,720,636 A | 1/1988 | Benner, Jr. |
| 4,763,032 A | 8/1988 | Bramm et al. |
| 4,772,273 A | 9/1988 | Alchas |
| 4,785,322 A | 11/1988 | Harrison et al. |
| 4,788,444 A | 11/1988 | Williams |
| 4,792,424 A | 12/1988 | Loman |
| 4,797,655 A | 1/1989 | Orndal et al. |
| 4,806,751 A | 2/1989 | Abe et al. |
| 4,845,487 A | 7/1989 | Frantz et al. |
| 4,845,489 A | 7/1989 | Hormel |
| 4,850,807 A | 7/1989 | Frantz |
| 4,878,896 A | 11/1989 | Garrison et al. |
| 4,882,575 A | 11/1989 | Kawahara |
| 4,884,013 A | 11/1989 | Jackson et al. |
| 4,884,065 A | 11/1989 | Crouse et al. |
| 4,909,797 A | 3/1990 | Timothy |
| 4,913,703 A | 4/1990 | Pasqualucci et al. |
| 4,933,563 A | 6/1990 | Thus |
| 4,940,050 A | 7/1990 | Forssmann et al. |
| 4,944,748 A | 7/1990 | Bramm et al. |
| 4,945,244 A | 7/1990 | Castleman |
| 4,950,235 A | 8/1990 | Slate et al. |
| 4,958,910 A | 9/1990 | Taylor et al. |
| 4,976,590 A | 12/1990 | Baldwin |
| 5,055,001 A | 10/1991 | Natwick et al. |
| 5,057,081 A | 10/1991 | Sunderland |
| 5,058,970 A | 10/1991 | Schildkraut et al. |
| 5,101,711 A | 4/1992 | Durbin |
| 5,181,842 A | 1/1993 | Sunderland et al. |
| 5,201,711 A | 4/1993 | Pasqualucci et al. |
| 5,207,645 A | 5/1993 | Ross et al. |
| 5,211,626 A | 5/1993 | Frank et al. |
| 5,237,450 A | 8/1993 | Stromberg |
| 5,250,027 A | 10/1993 | Lewis et al. |
| 5,256,155 A | 10/1993 | Yerlikaya et al. |
| 5,330,431 A | 7/1994 | Herskowitz |
| 5,336,174 A | 8/1994 | Daoud et al. |
| 5,352,364 A | 10/1994 | Kruger et al. |
| 5,357,113 A | 10/1994 | Liston et al. |
| 5,364,364 A | 11/1994 | Kasvikis et al. |
| 5,383,858 A | 1/1995 | Reilly et al. |
| 5,415,641 A | 5/1995 | Yerlikaya et al. |
| 5,433,588 A | 7/1995 | Monk et al. |
| 5,436,455 A | 7/1995 | Rosenthal et al. |
| 5,437,635 A | 8/1995 | Fields et al. |
| 5,502,111 A | 3/1996 | Huynh-Ba |
| 5,508,521 A | 4/1996 | Kraft et al. |
| 5,531,680 A | 7/1996 | Dumas et al. |
| 5,531,697 A | 7/1996 | Olsen et al. |
| 5,533,453 A | 7/1996 | Wolfberg et al. |
| 5,536,935 A | 7/1996 | Klotzsch et al. |
| 5,560,355 A | 10/1996 | Merchant et al. |
| 5,567,120 A | 10/1996 | Hungerford et al. |
| 5,569,026 A | 10/1996 | Novak |
| 5,575,284 A | 11/1996 | Athan et al. |
| 5,584,671 A | 12/1996 | Schweitzer, Jr. et al. |
| 5,586,567 A | 12/1996 | Smith et al. |
| 5,602,664 A | 2/1997 | Doyle |
| 5,604,020 A | 2/1997 | Fitchmun |
| 5,620,312 A | 4/1997 | Hyman et al. |
| 5,623,907 A | 4/1997 | Cotton et al. |
| 5,626,129 A | 5/1997 | Klimm et al. |
| 5,631,730 A | 5/1997 | Chupp et al. |
| 5,634,907 A | 6/1997 | Rani et al. |
| 5,661,231 A | 8/1997 | Koskela |
| 5,681,284 A | 10/1997 | Herskowitz |
| 5,683,367 A | 11/1997 | Jordan et al. |
| 5,704,912 A | 1/1998 | Lawrence et al. |
| 5,711,654 A | 1/1998 | Afflerbaugh |
| 5,721,430 A | 2/1998 | Wong |
| 5,752,813 A | 5/1998 | Tyner et al. |
| 5,767,976 A | 6/1998 | Ankerhold et al. |
| 5,788,674 A | 8/1998 | McWilliams |
| 5,795,327 A | 8/1998 | Wilson et al. |
| 5,798,699 A | 8/1998 | Bryant et al. |
| 5,818,049 A | 10/1998 | Bailey et al. |
| 5,828,458 A | 10/1998 | Taylor et al. |
| 5,851,631 A | 12/1998 | Borden et al. |
| 5,853,386 A | 12/1998 | Davis et al. |
| 5,882,338 A | 3/1999 | Gray |
| 5,903,006 A | 5/1999 | Kiuchi et al. |
| 5,920,018 A | 7/1999 | Wilkerson et al. |
| 5,974,708 A | 11/1999 | Webb et al. |
| 6,013,020 A | 1/2000 | Meloul et al. |
| 6,015,272 A | 1/2000 | Antaki et al. |
| 6,017,326 A | 1/2000 | Pasqualucci et al. |
| 6,023,970 A | 2/2000 | Blaine |
| 6,067,463 A | 5/2000 | Jeng et al. |
| 6,078,042 A | 6/2000 | Fellows |
| 6,095,986 A | 8/2000 | Braig et al. |
| 6,099,502 A | 8/2000 | Duchon et al. |
| 6,106,498 A | 8/2000 | Friedli et al. |
| 6,117,115 A | 9/2000 | Hill et al. |
| 6,129,699 A | 10/2000 | Haight et al. |
| 6,162,183 A | 12/2000 | Hoover |
| 6,219,138 B1 | 4/2001 | Swanson et al. |
| 6,227,817 B1 | 5/2001 | Paden |
| 6,244,835 B1 | 6/2001 | Antaki et al. |
| 6,263,227 B1 | 7/2001 | Boggett et al. |
| 6,299,600 B1 | 10/2001 | Masaoka et al. |
| 6,325,422 B1 | 12/2001 | Verkaart et al. |
| 6,390,590 B1 | 5/2002 | Hansburg |
| 6,437,316 B1 | 8/2002 | Colman et al. |
| 6,461,323 B2 | 10/2002 | Fowler et al. |
| 6,494,692 B1 | 12/2002 | Green |
| 6,523,414 B1 | 2/2003 | Malmstrom et al. |
| 6,528,791 B1 | 3/2003 | Williams et al. |
| 6,531,708 B1 | 3/2003 | Malmstrom et al. |
| 6,552,145 B1 | 4/2003 | Okada et al. |
| 6,585,684 B1 | 7/2003 | Hughett et al. |
| 6,617,175 B1 | 9/2003 | Arno |
| 6,626,862 B1 | 9/2003 | Duchon et al. |
| 6,659,976 B2 | 12/2003 | Beck et al. |
| 6,661,482 B2 | 12/2003 | Hara |
| 6,683,679 B2 | 1/2004 | Belenkii |
| 6,747,276 B2 | 6/2004 | Watanabe |
| 6,786,879 B1 | 9/2004 | Bolam et al. |
| 6,811,382 B2 | 11/2004 | Buchanan et al. |
| 6,890,291 B2 | 5/2005 | Robinson et al. |
| 6,891,343 B2 | 5/2005 | Petersen |
| 6,900,449 B2 | 5/2005 | Bolash et al. |
| 6,949,066 B2 | 9/2005 | Bearnson et al. |
| 6,958,053 B1 | 10/2005 | Reilly |
| 7,009,150 B2 | 3/2006 | Wennemann et al. |
| 7,018,363 B2 | 3/2006 | Cowan et al. |
| 7,041,082 B2 | 5/2006 | Blomquist et al. |
| 7,092,796 B2 | 8/2006 | Vanderveen |
| 7,126,495 B2 | 10/2006 | Netzer |
| 7,144,384 B2 | 12/2006 | Gorman et al. |
| 7,145,127 B2 | 12/2006 | Chin et al. |
| 7,258,534 B2 | 8/2007 | Fathallah et al. |
| 7,462,170 B2 | 12/2008 | Fournie et al. |
| 7,537,579 B2 | 5/2009 | Price |
| 7,560,686 B2 | 7/2009 | Bisch et al. |
| 7,570,428 B2 | 8/2009 | Watanabe |
| 7,578,782 B2 | 8/2009 | Miles et al. |
| 7,591,980 B2 | 9/2009 | Call et al. |
| 7,608,059 B2 | 10/2009 | Harr et al. |
| 7,632,248 B2 | 12/2009 | Delk et al. |
| 7,682,345 B2 | 3/2010 | Savage |
| 7,722,562 B2 | 5/2010 | Hanlon et al. |
| 7,722,573 B2 | 5/2010 | Harr et al. |
| 7,758,551 B2 | 7/2010 | Wiesner et al. |
| 7,763,005 B2 | 7/2010 | Knauper et al. |
| 7,807,982 B2 | 10/2010 | Nishiuchi et al. |

(56) References Cited

U.S. PATENT DOCUMENTS

| | | |
|---|---|---|
| 7,927,304 B2 | 4/2011 | Hudson et al. |
| 8,142,404 B2 | 3/2012 | Knauper et al. |
| 2002/0036276 A1 | 3/2002 | Seeman |
| 2004/0036273 A1 | 2/2004 | McClary |
| 2005/0186377 A1 | 8/2005 | Hurst et al. |
| 2005/0267401 A1 | 12/2005 | Price et al. |
| 2006/0268493 A1 | 11/2006 | Miyasaka et al. |
| 2008/0147008 A1 | 6/2008 | Lewis et al. |
| 2009/0284603 A1 | 11/2009 | Hsieh |
| 2010/0198144 A1 | 8/2010 | Knauper et al. |
| 2010/0198145 A1 | 8/2010 | Hanlon et al. |

FOREIGN PATENT DOCUMENTS

| | | |
|---|---|---|
| EP | 0467805 B1 | 3/1995 |
| EP | 0563351 B1 | 12/1997 |
| EP | 0718006 B1 | 3/1999 |
| EP | 0891784 B1 | 9/2003 |
| EP | 0876825 B1 | 2/2005 |
| EP | 1941923 A1 | 7/2008 |
| EP | 1542742 B1 | 3/2010 |
| EP | 1932555 B1 | 6/2010 |
| ES | 8500067 A1 | 1/1985 |
| GB | 2065916 A | 7/1981 |
| JP | 2006233014 A | 9/2006 |
| JP | 2008212314 A | 9/2008 |
| WO | 93/20440 A1 | 10/1993 |
| WO | 93/20441 A1 | 10/1993 |
| WO | 95/08774 A2 | 3/1995 |
| WO | 98/44320 A1 | 10/1998 |

OTHER PUBLICATIONS

Office action issued Apr. 19, 2010 in related U.S. Appl. No. 11/649,981 now issued as Patent No. 8,021,336—7 pgs.
Response filed May 18, 2010 to Office Action dated Apr. 19, 2010 regarding related U.S. Appl. No. 11/649,981 now issued as Patent No. 8,021,336—7 pgs.
Office action issued Jun. 10, 2010 in related U.S. Appl. No. 11/649,981 now issued as Patent No. 8,021,336—9 pgs.
Response filed Aug. 13, 2010 to Office Action dated Jun. 10, 2010 regarding related U.S. Appl. No. 11/649,981 now issued as Patent No. 8,021,336—13 pgs.
Office action issued Sep. 28, 2010 in related U.S. Appl. No. 11/649,981 now issued as Patent No. 8,021,336—10 pgs.
Response filed Nov. 29, 2010 to Office Action dated Sep. 28, 2010 regarding related U.S. Appl. No. 11/649,981 now issued as Patent No. 8,021,336—12 pgs.
Advisory Action issued Dec. 8, 2010 in related U.S. Appl. No. 11/649,981 now issued as Patent No. 8,021,336—2 pgs.
Response filed Dec. 27, 2010 to Advisory Action dated Dec. 8, 2010 regarding related U.S. Appl. No. 11/649,981 now issued as Patent No. 8,021,336—15 pgs.
Office action issued Apr. 13, 2011 regarding U.S. Appl. No. 12/757,193—7 pgs.
Response filed Jul. 13, 2011 to Office Action dated Apr. 13, 2011 regarding U.S. Appl. No. 12/757,193—11 pgs.
Office action issued Oct. 6, 2011 regarding U.S. Appl. No. 12/757,193—8 pgs.
Response filed Dec. 1, 2011 to Office Action dated Oct. 6, 2011 regarding U.S. Appl. No. 12/757,193—2 pgs.
Office action issued Sep. 1, 2011 regarding U.S. Appl. No. 12/777,357—8 pgs.
Response filed Dec. 1, 2011 to Office Action dated Sep. 1, 2011 regarding U.S. Appl. No. 12/777,357—11 pgs.
Garcia, et al: Computational Prediction of PVC Degradation During Injection Molding in a Rectangular Channel, Polymer Engineering & Science, Jul. 2004, vol. 44, No. 7, pp. 1295-1312, Society of Plastics Engineers, United States.
Compat Yset consisting of four photographs and description, publication date unknown but admitted as prior art, 5 pgs, Nov. 19, 2012.
Exam Report from corresponding European Application No. 11003184.6 dated Apr. 11, 2013, 4 pgs.
Supplemental response filed Apr. 26, 2013 to Office Action dated Jan. 3, 2013 from related U.S. Appl. No. 13/211,423, 16 pgs.
Office Action from corresponding European Application No. 11003184.6 dated Oct. 24, 2013, 5 pages.
Chinese Office Action dated Jan. 6, 2014 in related Chinese Application No. 201110119053.1, 6 pages.
Office Action dated Dec. 31, 2013 in related Israel Application No. 212336, 3 pages.

SAFETY INTERLOCK

CROSS REFERENCE TO RELATED APPLICATION

This application is a continuation application of and claims the benefit of priority under 35 U.S.C. §120 to U.S. patent application Ser. No. 12/777,357, filed May 11, 2010, which is hereby incorporated by reference for all purposes.

FIELD OF THE INVENTION

The present invention generally relates to a pump set for delivering fluids to a patient by way of a flow control apparatus, and more particularly to a pump set having a safety interlock device for determining secure loading of the pump set on the flow control apparatus.

BACKGROUND OF THE INVENTION

Administering fluids containing medicine or nutrition to a patient is well known in the art. Fluids can be delivered to patients by gravity flow, but often are delivered to the patient by a pump set loaded on a flow control apparatus, such as a peristaltic pump, which delivers fluid to the patient at a controlled rate of delivery. A peristaltic pump usually comprises a housing that includes a rotor or the like operatively engaged to at least one motor through a gearbox. The rotor drives fluid through the tubing of the pump set by the peristaltic action effected by rotation of the rotor by the motor. The motor is operatively connected to a rotatable shaft that drives the rotor, which in turn progressively compresses the tubing and drives the fluid at a controlled rate through the pump set. A controller operates the motor to drive the rotor. Other types of peristaltic pumps not employing rotors are also known.

In order for the pump to deliver an accurate amount of fluid corresponding with the flow parameters programmed into the pump, the administration feeding set must be correctly loaded on the pump. If the pump set is misaligned in the pump, the pump may deliver an inaccurate amount of fluid to a patient or the pump generates a low flow alarm requiring the condition to be examined and the set reloaded. Existing pumps have systems to detect whether the pump set is properly loaded. An example of such a pump having a detection system is shown in co-assigned U.S. Pat. No. 4,913,703, entitled SAFETY INTERLOCK SYSTEM FOR MEDICAL FLUID PUMPS and U.S. Publication No. 2007/0253833, entitled PUMP SET WITH SAFETY INTERLOCK, the disclosures of which are incorporated by reference.

SUMMARY OF THE INVENTION

In one aspect, a safety interlock for use in a medical device having a control system for controlling operation of the medical device generally comprises a central tubular portion defining a fluid passage for passing fluid through the safety interlock. An outer ring portion is adapted for mounting the safety interlock in the medical device. A spoked connector portion connects the central tubular portion to the outer ring portion so that the outer ring portion is spaced radially outwardly from the central tubular portion in opposed relation with at least a portion of the central tubular portion. The safety interlock is adapted for mounting in the medical device in a path of electromagnetic radiation from a source of electromagnetic radiation such that the central tubular portion reflects the electromagnetic radiation to an electromagnetic radiation detector when properly loaded in the medical device.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
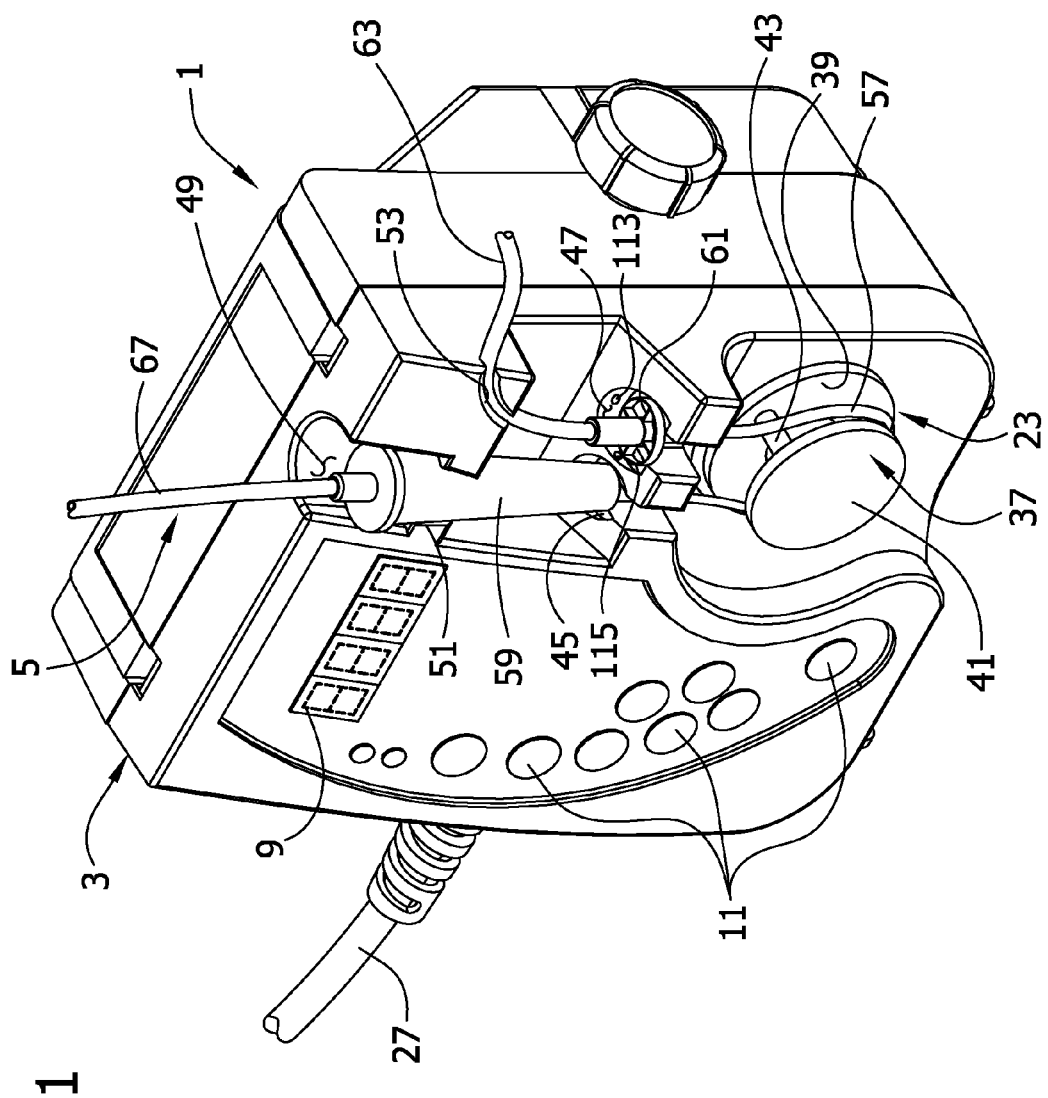
FIG. 1 is a perspective of an enteral feeding pump showing a fragmentary portion of a feeding set loaded in the pump.

Referring now to the drawings, an enteral feeding pump (broadly, "a pumping apparatus") constructed according to the principles of the present invention is generally indicated at 1. The feeding pump comprises a housing generally indicated at 3 that is constructed so as to mount an administration feeding set (broadly, a "pump set") generally indicated at 5 (see FIGS. 1 and 3). It will be appreciated that "housing" as used herein may include many forms of supporting structures (not shown), including without limitation multi-part structures and structures that do not enclose or house the working components of the pump 1. The pump 1 also has a display screen 9 on the front of the housing 3 that is capable of displaying information about the status and/or operation of the pump. Buttons 11 on the side of the display screen 9 are provided for use in controlling and obtaining information from the pump 1. It will be understood that although the illustrated pump 1 is an enteral feeding pump, the present invention has application to other types of peristaltic pumps (not shown), including medical infusion pumps. A pump of the same general type as described herein is shown in co-assigned U.S. Pat. No. 4,909,797 entitled ENTERAL DELIVERY SET WITH SHADED DRIP CHAMBER, the disclosure of which is incorporated herein by reference.

Figure 4:
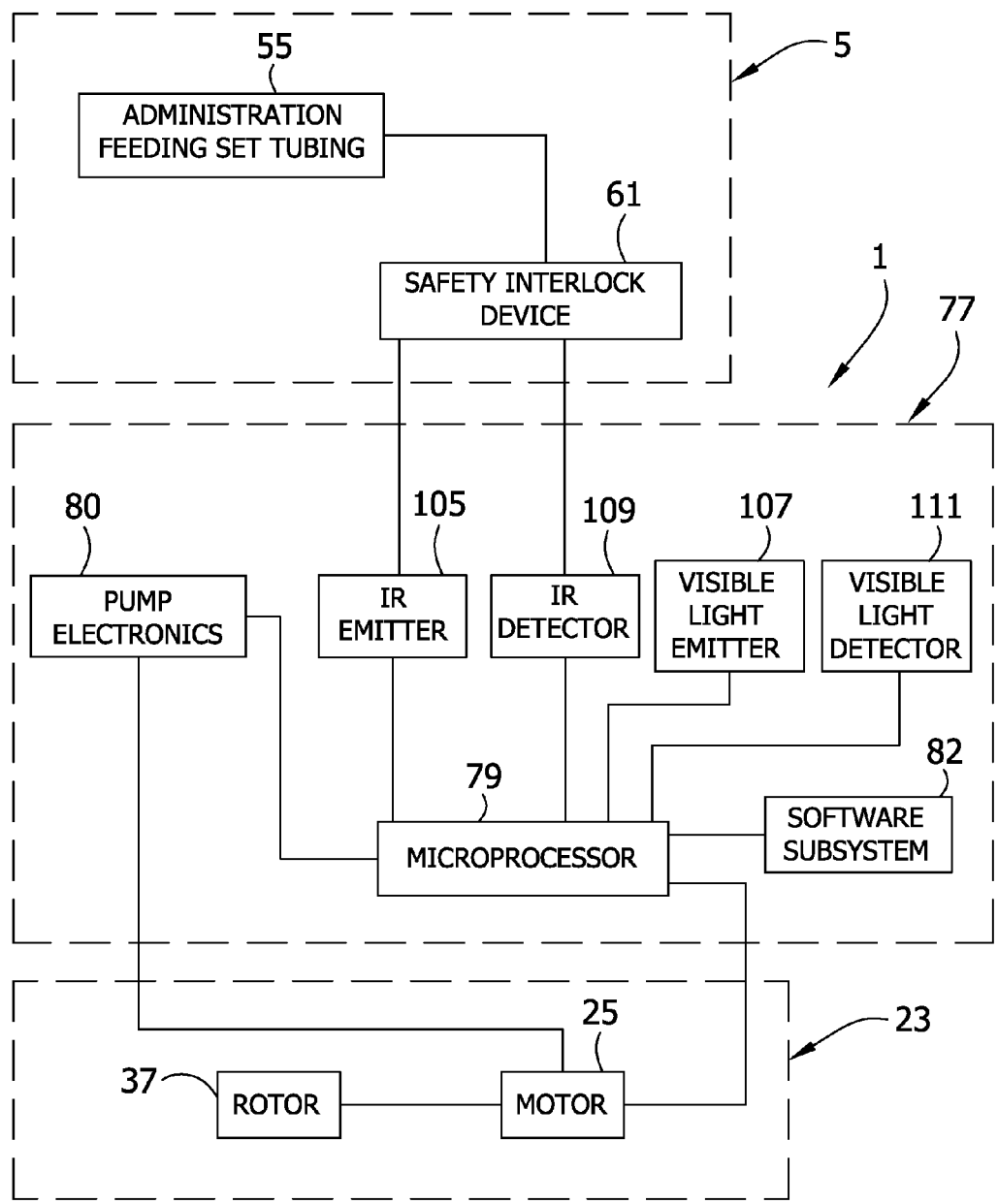
FIG. 4 is a block diagram showing the elements of the pump and feeding set.

The enteral feeding pump 1 further includes a pumping unit (indicated generally at 23) comprising a pump motor 25 located in the housing 3 and shown schematically in FIG. 4. An electrical cord 27 extends from the housing 3 for connection to a source of electrical power for the motor 25. Alternatively, or in addition, a battery (not shown) may be received in the housing 3 for powering the pump motor 25. The pumping unit 23 further includes a rotor (generally indicated at 37) mounted on a rotor shaft (not shown) of the pumping unit. The rotor 37 includes an inner disk 39, an outer disk 41 and three rollers 43 (only one is shown) mounted between the inner and outer disks for rotation about their longitudinal axes relative to the disks. In the illustrated embodiment, the pump motor 25, rotor shaft and rotor 37 may broadly be considered "a pumping device". The pump housing 3 includes a first lower recess 45 above the rotor 37 and a second lower recess 47 generally adjacent the first lower recess. The housing 3 has an upper recess 49 generally axially aligned with the first lower recess 45 and a shoulder 51 at the bottom of the upper recess for receiving and holding part of the feeding set 5. A curved recess 53 in the housing 3 above the second lower recess 47 receives and holds another part of the administration feeding set 5 in place. The lower recesses 45, 47, upper recess 49 and curved recess 51 may broadly be considered, individually or as a group, "a receiving portion" of the housing 3 that receives parts of the administration feeding set 5 in a manner that will be described in more detail hereinafter.

Figure 3:
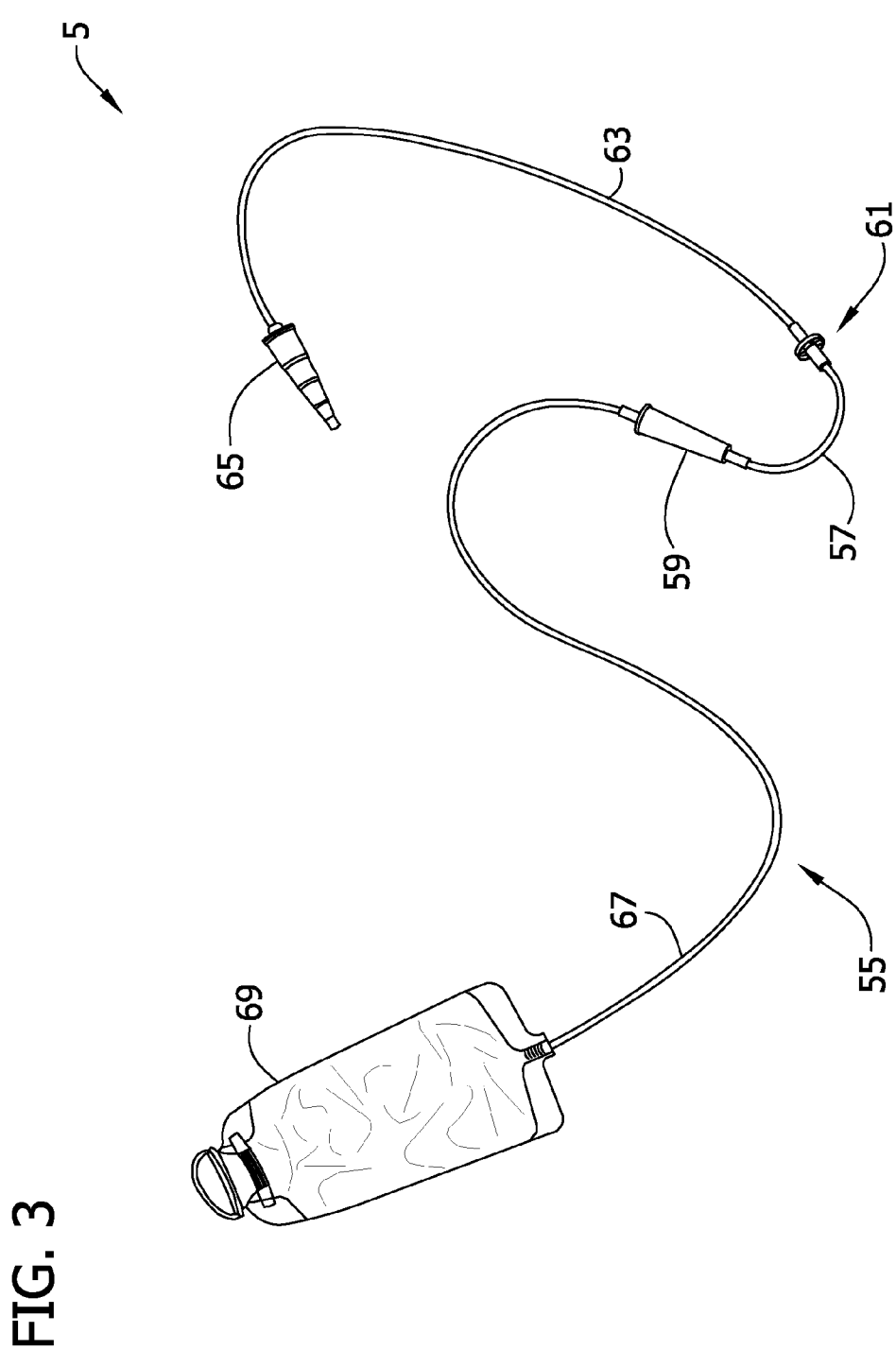
FIG. 3 is an elevation of the administration feeding set.

Referring now to FIG. 3, the administration feeding set 5 comprises tubing (broadly, "a conduit") indicated generally at 55 that provides a fluid pathway between at least one source of fluid and a patient. Tubing 55 can be made of a medical grade, deformable silicone and comprises first tube section 57 connected between a drip chamber 59 and a safety interlock device, generally indicated at 61. A second tube section 63 is connected to the safety interlock device 61 and at an outlet of the tubing 55 to a connector, such as a barbed connector 65, suitable for connection to a gastrostomy device (not shown) attached to a patient. Third tube section 67 is connected at an inlet of the tubing 55 to a bag 69 of nutrient liquid and to the drip chamber 59. As previously stated, pump sets of different constructions may be used, for example a recertification set (not shown) may be used to verify and/or correct the pump accuracy. The pump 1 can be configured to automatically recognize what kind of set is installed and to alter its operation to conform to that called for by the particular pump set. Still further, the pump 1 can be configured to detect with sensors whether the first tube section 57 is properly installed on the pump.

Figure 5:
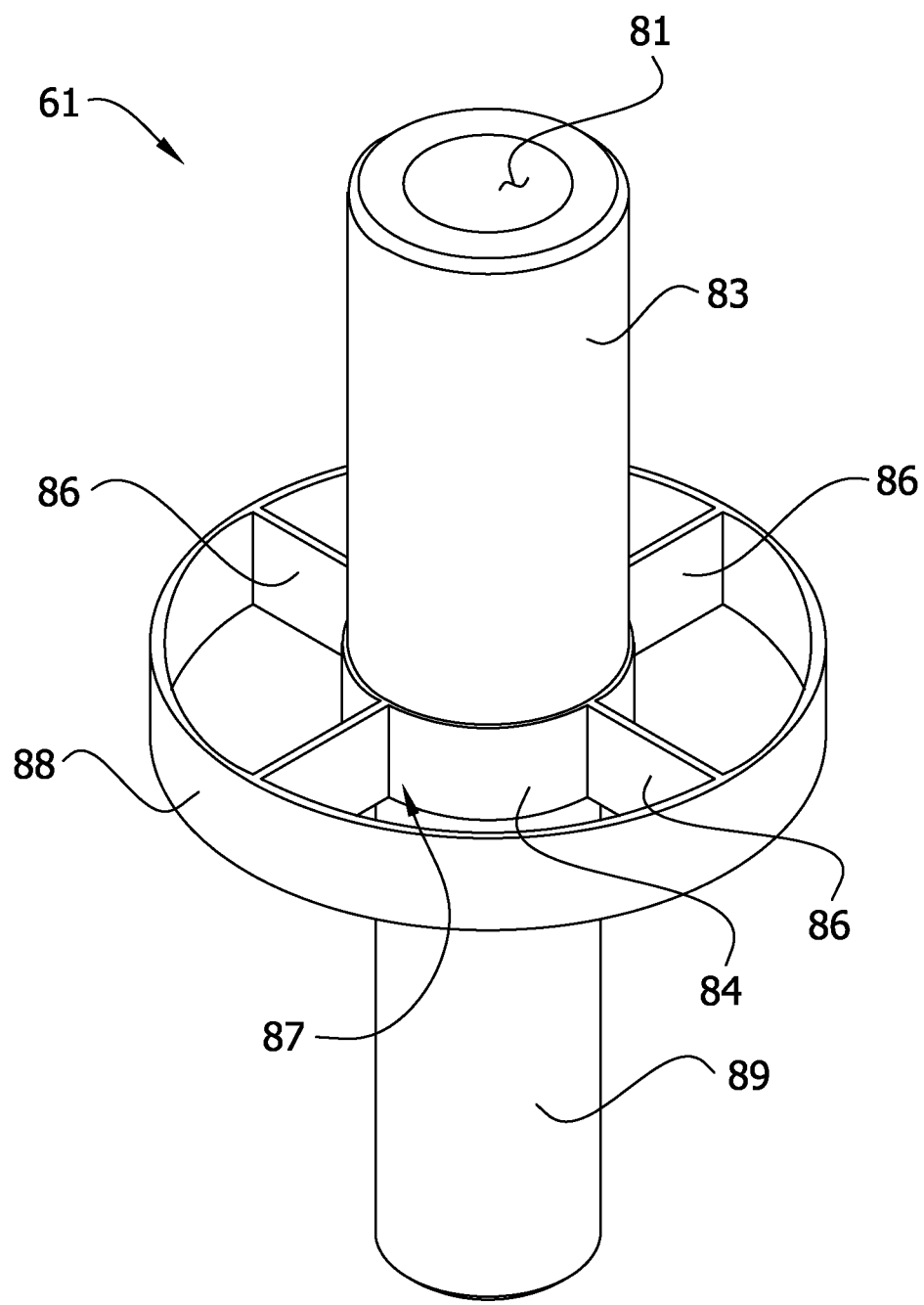
FIG. 5 is a perspective of a safety interlock device of the present invention.
Figure 6:
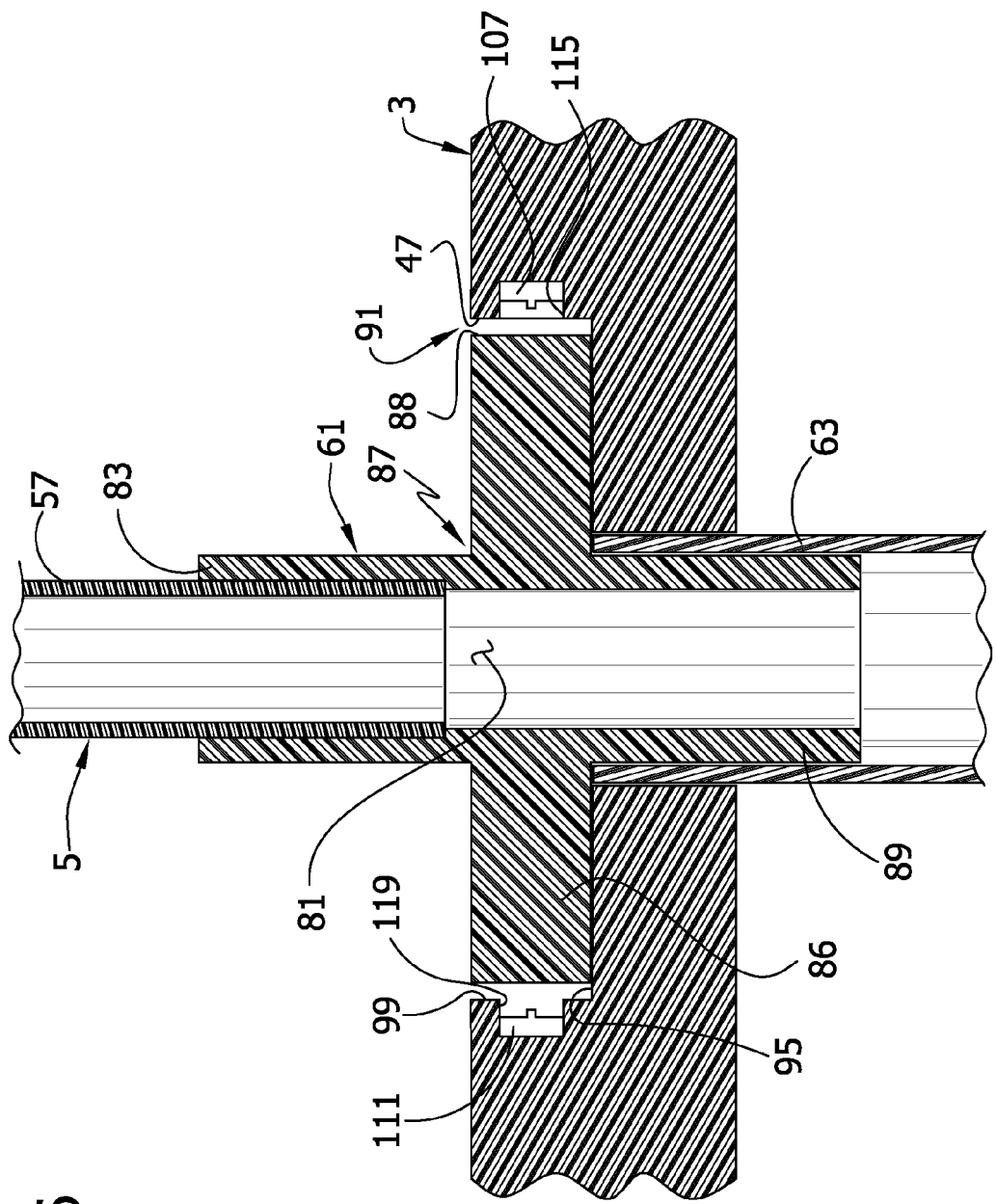
FIG. 6 is an enlarged, fragmentary section of the pump and safety interlock device.

As shown in FIG. 3, the safety interlock device 61 connects first tube section 57 and the second tube section 63 of the administration feeding set 5. The safety interlock device 61 has a central axial bore 81 to allow the flow of fluid between the first tube section 57 and the second tube section 63 (FIG. 6). Referring to FIGS. 5 and 6, the safety interlock device 61 has an upper central tubular portion 83 that receives a portion of the tube 57 and a lower central tubular portion 89 that is received in the second tube section 63 for attaching the second tube section to the safety interlock device. A spoked connector portion 87 extends radially outwardly from the central tubular portions 83, 89 to an outer ring portion 88. The spoked connector portion 87 includes a connector ring 84 received around the central tubular portions 83, 89 and spokes 86 extending radially outwardly from the connector ring to the outer ring portion 88. Thus, the outer ring portion 88 is spaced radially outwardly from the central tubular portions 83, 89 and in opposed relation with at least a portion of the central tubular portions. It is to be understood that the safety interlock device 61, and in particular the central tubular portions 83, 89 may be separate from the administration feeding set 5, and/or may be attached to the administration feeding set in such a way that liquid does not pass through the safety interlock device.

Figure 2:
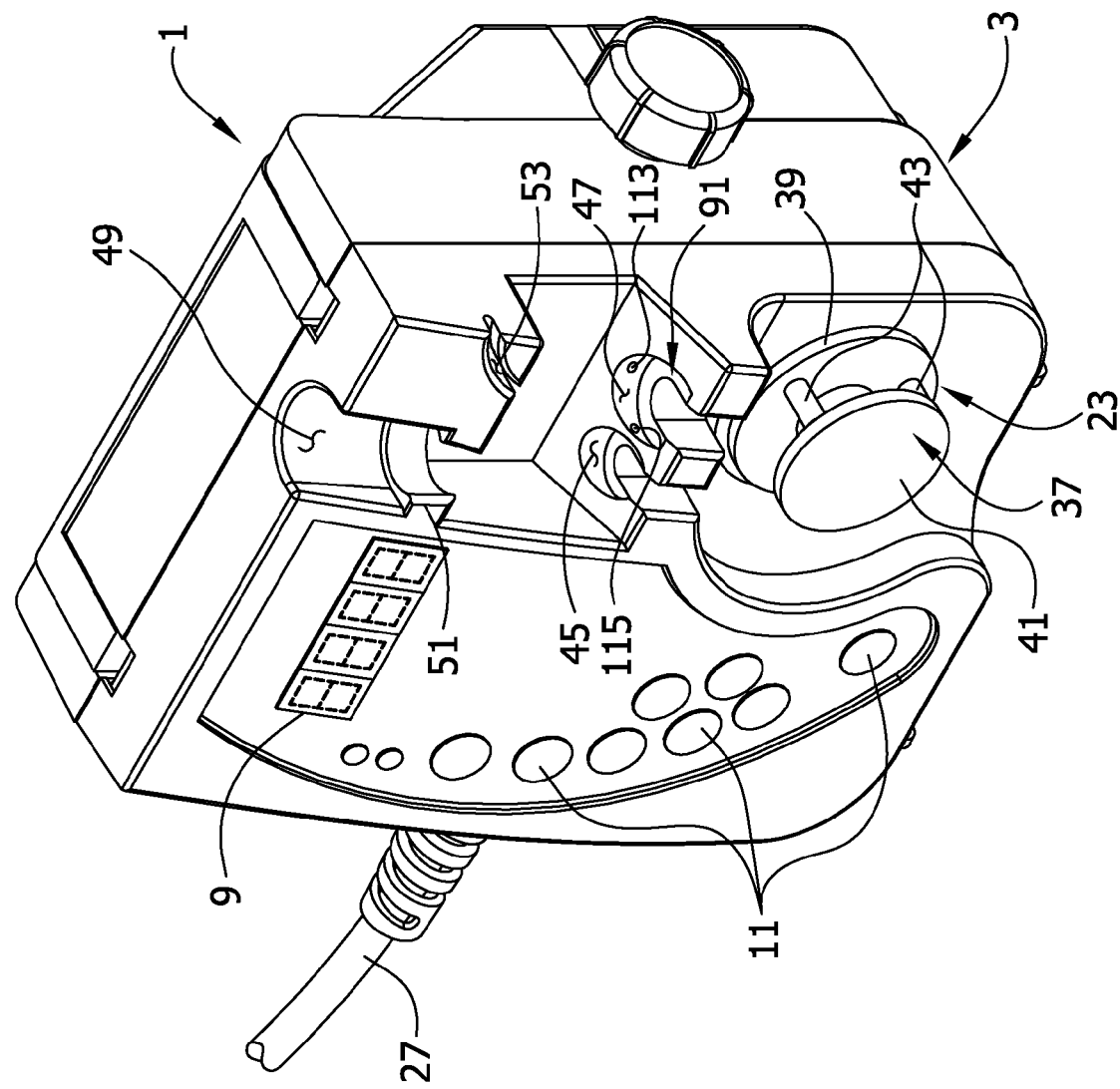
FIG. 2 is a perspective of the pump without the feeding set.

The outer ring potion 88 is sized to be received on a seat, indicated generally at 91 (FIG. 2), formed at the bottom of the second lower recess 47 in the pump 1 when the administration feeding set 5 is properly loaded on the pump (FIG. 1). In the illustrated embodiment, the seat 91 is generally semi-cylindrical to correspond with the shape of the safety interlock device 61 and includes an axially facing surface 95 in the second lower recess 47 and a radially facing surface 99 in the second lower recess 47. In this embodiment, proper functioning of the pump 1 is generally achieved when the central tubular portions 83, 89 are seated in substantially face-to-face relation with the axially facing surface 95 of the seat 91. The rotational orientation of the safety interlock 61, within the seat 91, about its axis is generally not pertinent to operation.

Other ways of positioning the safety interlock 61 may be used within the scope of the present invention. The safety interlock device 61 and the seat 91 in the housing 3 may be shaped to prevent the administration feeding set 5 from being accidentally dislodged and to prevent the use of non-compliant feeding sets that do not have the safety interlock device. In the illustrated embodiment, the safety interlock device 61 and seat 91 are generally cylindrical in shape but it is understood that other shapes (e.g., hex-shaped) may be used for the safety interlock device and the seat.

The pump 1 can be programmed or otherwise controlled for operation in a desired manner. For instance, the pump 1 can begin operation to provide feeding fluids from bag 69 to the patient. The care giver may select, for example, the amount of fluid to be delivered, the rate at which the fluid is to be delivered and the frequency of fluid delivery. As shown in FIG. 4, the pump 1 has a controller 77 (broadly, "a control system") including a microprocessor 79 that allows it to accept programming and/or to include pre-programmed operational routines that can be initiated by the care giver. The microprocessor 79 controls pump electronics 80 that operate the motor 25. A software subsystem 82 is used to determine if the feeding set 5 has been positioned properly on the pump 1.

Figure 7:
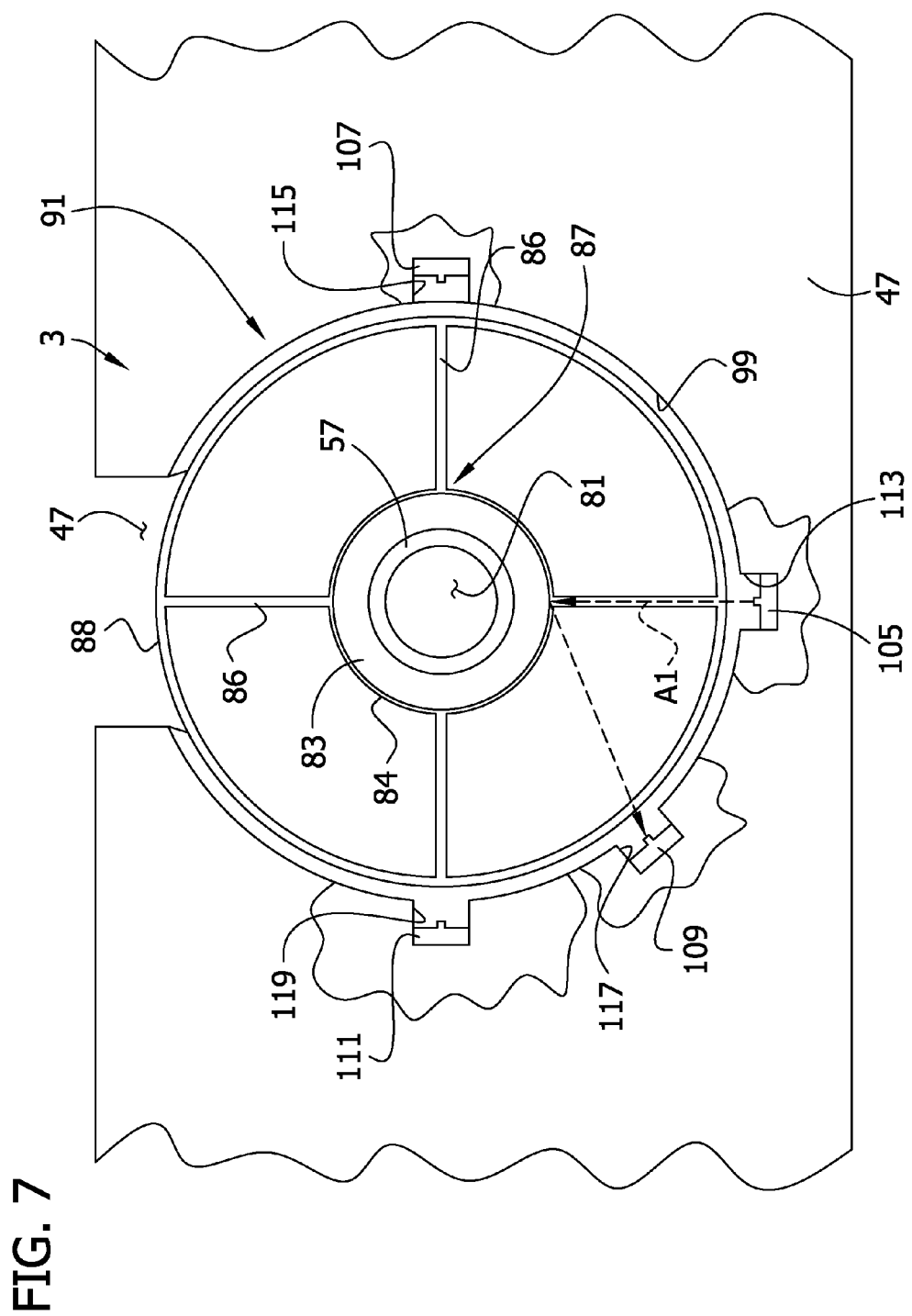
FIG. 7 is a top plan view of FIG. 6.

Referring to FIGS. 4, 6 and 7, the pump 1 includes an infrared ("IR") emitter 105 (broadly, "a source of electromagnetic radiation") housed in the second lower recess 47. The IR emitter 105 is operatively connected to the controller 77 for emitting an electromagnetic signal having a ("first") wavelength in the infrared range in a direction for striking the safety interlock device 61 of the feeding set 5. In the illustrated embodiment, the source of electromagnetic radiation is an infrared (IR) emitter 105 but it is understood that other types of sources of electromagnetic radiation may be used without departing from the scope of this invention. An infrared ("IR") detector 109 located in the second lower recess 47 is operatively connected to the controller 77 for receiving the infrared signal from the IR emitter 105 and providing an indication to the controller that the feeding set 5 is properly positioned in the pump 1. In the illustrated embodiment, the IR detector 109 (broadly, "a first sensor") detects infrared radiation but it is understood that electromagnetic radiation sensors that detect other types of electromagnetic radiation may be used without departing from the scope of this invention. The IR detector 109 distinguishes infrared radiation from other types of electromagnetic radiation (e.g., visible or ultraviolet light).

A visible light emitter 107 (broadly, "a second source of electromagnetic radiation") may be housed in the second lower recess 47. The visible light emitter 107 is operatively connected to the controller 77 for emitting an electromagnetic signal having a ("second") wavelength in the visible range in a direction for striking the safety interlock device 61 of the feeding set 5. In the illustrated embodiment, the source of electromagnetic radiation is a visible light emitter 107 but it is understood that other types of sources of electromagnetic radiation may be used without departing from the scope of this invention. A visible light detector 111 (broadly, "a second electromagnetic radiation detector" and "a second sensor") is housed in the second lower recess 47 generally adjacent the IR detector 109 and opposite the visible light emitter 107. The visible light detector 111 provides a signal to the controller 77 when visible light from the surrounding environment (e.g., electromagnetic radiation of a second wavelength) is detected to indicate that the safety interlock device 61 is not mounted in the second lower recess 47 in a position that blocks visible light from reaching the detector. Preferably, the visible light detector 111 is configured to detect electromagnetic radiation in the visible range, but not to detect electromagnetic radiation outside the visible range (e.g., infrared radiation). A second electromagnetic radiation detector could be configured to detect electromagnetic radiation in other ranges, such as in the ultraviolet range. Thus, the visible light detector 111 can distinguish visible light from infrared radiation. As used herein, electromagnetic radiation of a "first" or "second" wavelength is intended in each case to encompass a range of wavelengths, such as wavelengths falling in the infrared range, visible range and/or ultraviolet range.

Other sensors (not shown), such as a sensor that determines the type of pump set that has been placed in the pump 1 and a flow monitoring sensor can be in communication with the controller 77 to facilitate accurate operation of the pump. The IR emitter 105 is positioned in an alcove 113 in the second lower recess 47 of the housing 3 so that electromagnetic radiation (indicated by arrows A1 in FIG. 7) from the emitter is directed to the upper central tubular portion 83 of the safety interlock device 61 (see also, FIG. 6). When the safety interlock device 61 is properly located on the seat 91, the infrared radiation from the IR emitter 105 is reflected off of the upper central tubular portion 83 so that the infrared radiation is directed to and detected by the IR detector 109. The connector portion 87 and outer ring portion 88 are disposed generally within a common horizontal plane when the safety interlock 61 is mounted in the pump 1. In the illustrated embodiment, the connector portion 87 and outer ring portion 88 are located out of the path of, or above, the radiation emitted from the IR emitter 105 when the safety interlock 61 is properly located on the seat 91. However, the connector portion 87 and outer ring portion could be located in the path of the radiation emitted from the IR emitter 105 or below the IR emitter.

The IR detector is positioned in an alcove 117 in the radially facing surface 99 of the seat 91, the visible light emitter 107 is positioned in an alcove 115, and the visible light detector 111 is positioned in an alcove 119. The alcoves 113, 115, 117, 119 recess the IR emitter 105, visible light emitter 107, and the IR and visible light detectors 109, 111 to protect them from physical contact with the safety interlock device 61. Although not shown, a clear plastic window may enclose each of the emitters 105, 107 and the detectors 109, 111 within their corresponding alcoves 113, 115, 117, 119 for additional protection. Moreover, the alcoves 117 and 119 help to shield the detectors 109 and 111 from ambient electromagnetic radiation (which may include both visible light and infrared radiation).

In the illustrated embodiment, the IR emitter 105 is located approximately 49 degrees from the IR detector 109. When the feeding set 5 is not loaded in the second lower recess 47 and the safety interlock device 61 is not received on the seat 91, the infrared radiation from the IR emitter 105 is not detected by the IR detector 109. Also when the safety interlock device 61 is not received on the seat 91, visible light from outside of the pump 1 (i.e., ambient light) and/or visible light from the visible light emitter 107 may enter the second lower recess 47 and is detected by the visible light detector 111. The central tubular portions 83, 89 are preferably constructed of a material that reflects infrared radiation, but is opaque to visible light. The connector portion 87 and outer ring portion 88 are preferably constructed of a material that is transparent to infrared radiation and visible light such as clear plastic. However, the outer ring portion 88 and/or connector portion 87 could be made of material that will not transmit visible light, but will transmit infrared radiation. In the illustrated embodiment, the central tubular portions 83, 89 are monolithic or formed by a single piece construction. However, the central tubular portions 83, 89 could be formed from separate pieces and attached together by a suitable means.

Figure 8:
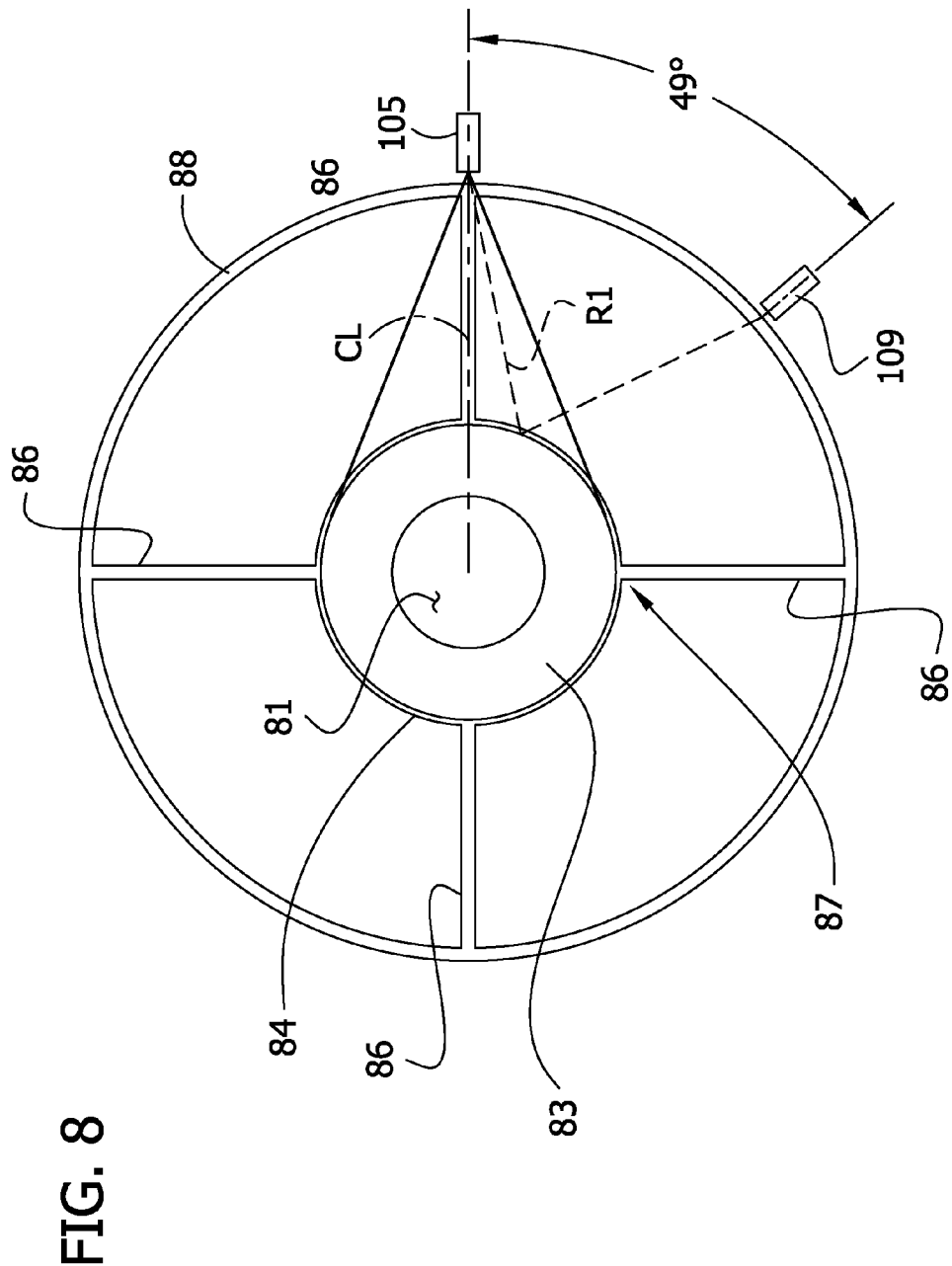
FIG. 8 is a schematic diagram of FIG. 7 showing the reflection of electromagnetic radiation off the safety interlock device.

Referring now to FIG. 8, reflection of infrared radiation off of the upper central tubular portion 83 is schematically illustrated. The IR emitter 105 emits infrared radiation in a cone toward the side of the upper central tubular portion 83. The IR emitter 105 is arranged generally perpendicular to the central tubular portions 83, 89. The centerline CL of the cone is denoted in the drawing. For simplicity, we will look at a ray R1 of radiation that is a bisector of approximately one half of the cone. The ray R1 is representative of the nominal path of infrared radiation in this half of the cone. The other half of the cone (i.e., that portion above the centerline CL in FIG. 8) is believed to be of small or no use in providing a light signal capable of being detected by the IR detector 109. The ray R1 strikes the side of the upper central tubular portion 83 at an angle. The ray R1 is reflected back toward the side of the recess 47. Finally, the ray R1 strikes the side of the recess 47 at a location that is about 49 degrees away from the location of the IR emitter 105. Accordingly, the IR detector 109 is preferably positioned here, or in a range of around 0-50 degrees. In another embodiment of the present invention (not shown), an IR detector is positioned about 60 degrees from the IR emitter.

In use, the administration feeding set feeding fluid bag 69 can be hung from a suitable support, such as an IV pole (not shown). The drip chamber 59 can be placed in the first lower recess 45 and upper recess 49 in an operating position as shown in FIG. 1. The first tube section 57 is placed around the lower part of the rotor 37 and the safety interlock device 61 is placed on the seat 91 at the bottom of the second lower recess 47. The seat 91 in the second lower recess 47 is generally located so that the safety interlock device 61 can be placed into the second lower recess at a location in which the first tube section 57 is substantially stretched around the rotor 37. The IR emitter 105 and IR detector 109 may intermittently or continuously check for the presence of the properly loaded feeding set 5. When the safety interlock device 61 is received in a proper operating position on the seat 91, the infrared signal from the IR emitter 105 is directed to the upper central tubular portion 83. The central tubular portion reflects the infrared signal from the IR emitter on to the IR detector 109 (see FIGS. 7 and 8). The IR detector is periodically operated and detects the presence of infrared radiation when the feeding set 5 has been properly loaded on the pump. It is understood that the IR detector 109 is preferably unable to detect electromagnetic radiation having a wavelength in the visible light region of the electromagnetic spectrum. Upon detection of the infrared signal, the IR detector 109 sends a corresponding signal to the microprocessor 79. Also, when the safety interlock device 61 is loaded onto the seat 91, visible light from ambient light and from the visible light emitter 107 is blocked by the central tubular portions 83, 89 from reaching the visible light detector 111. When the set 5 is loaded, the visible light detector 111 sends a signal to the microprocessor 79 to indicate that visible light is blocked and the pump 1 may be operated.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A safety interlock for use in a medical device having a control system for controlling operation of the medical device, a source of electromagnetic radiation operatively connected to the control system of the medical device for emitting electromagnetic radiation, and an electromagnetic radiation detector operatively connected to the control system for providing an indication that the safety interlock is properly loaded on the medical device, the safety interlock comprising:
   a central tubular portion defining a fluid passage for passing fluid through the safety interlock;
   an outer ring portion adapted for mounting the safety interlock in the medical device; and
   a spoked connector portion connecting the central tubular portion to the outer ring portion so that the outer ring portion is spaced radially outwardly from the central tubular portion in opposed relation with at least a portion of the central tubular portion;
   the safety interlock being adapted for mounting in the medical device in a path of the electromagnetic radiation from the source of electromagnetic radiation such that the central tubular portion reflects the electromagnetic radiation to the electromagnetic radiation detector when properly loaded in the medical device.

2. The safety interlock of claim 1, wherein the outer ring portion and the spoked connector portion are centered about a common horizontal plane extending orthogonal to a longitudinal axis of the central tubular portion when the safety interlock is mounted in the medical device.

3. The safety interlock of claim 2, wherein the outer ring portion does not inhibit propagation of the electromagnetic radiation from the source of electromagnetic radiation when the safety interlock is mounted in the medical device.

4. The safety interlock of claim 3, wherein the outer ring portion and the spoked connector portion are substantially transparent to both infrared radiation and visible light.

5. The safety interlock of claim 1, wherein the spoked connector portion comprises a connector ring received around the central tubular portion and spokes extending radially outwardly from the connector ring to the outer ring portion.

6. The safety interlock of claim 5, wherein the spoked connector portion comprises at least two spokes.

7. The safety interlock of claim 6, wherein the spoked connector portion comprises four spokes.

8. The safety interlock of claim 1, wherein the spoked connector portion is formed at least in part by two separate spokes.

9. The safety interlock of claim 1, in combination with the medical device.

* * * * *